United States Patent [19]

Westerhof et al.

[11] Patent Number: 5,204,103
[45] Date of Patent: Apr. 20, 1993

[54] USE OF POLYSACCHARIDES IN PREPARATION FOR WOUND TREATMENT

[75] Inventors: Wiete Westerhof, Landsmeer; Jacob Verschoor, Teteringen, both of Netherlands

[73] Assignee: Pharmalett International B.V., Teteringen, Netherlands

[21] Appl. No.: 751,336

[22] Filed: Aug. 29, 1991

[30] Foreign Application Priority Data

Sep. 7, 1990 [NL] Netherlands ............... 9001980

[51] Int. Cl.$^5$ ............... A61K 35/78; A61K 37/54; A61K 9/70
[52] U.S. Cl. ............... 424/195; 424/94.63; 424/443; 424/652; 514/54
[58] Field of Search ............... 424/195.1, 443, 94.63, 424/652; 514/54

[56] References Cited

U.S. PATENT DOCUMENTS

| 4,321,263 | 3/1982 | Powell et al. | 424/195.1 |
| 4,828,842 | 5/1989 | Furst et al. | 424/195.1 |
| 4,851,394 | 7/1989 | Kubodera | 514/54 |

FOREIGN PATENT DOCUMENTS

| 0209142 | 1/1987 | European Pat. Off. |
| 0273069 | 7/1988 | European Pat. Off. |
| 3444746 | 6/1985 | Fed. Rep. of Germany |
| 1207352 | 9/1970 | United Kingdom |

Primary Examiner—John W. Rollins
Attorney, Agent, or Firm—Bachman & Lapointe

[57] ABSTRACT

The invention relates to the use of polysaccharide containing materials in particular vegetable fibres or products derived therefrom originating from *Plantago ovata*, in particular from the seed husk thereof for the production of preparations for wound treatment. These and similar vegetable fibres or products derived therefrom may be combined with another active substance chosen from the group comprising proteolytic enzymes, antiseptic agents, growth stimulators and electrolytes.

10 Claims, 3 Drawing Sheets

+ psyllium    * krill 6.0 U/ml, 1986    × control (NaCl), 1986

USE OF POLYSACCHARIDES IN PREPARATION FOR WOUND TREATMENT

The invention relates to the use of polysaccharide-containing materials in preparations for wound treatment.

In the field of dermatology and surgery, secondary-healing ulcers are a great problem. In the case of such ulcers there is frequently devitalised tissue, pus or accumulation of fibrin and the granulation process and the formation of epithelium is delayed. Surgical cleaning (débridement) is traditionally used to remove necrotic material. Frequently, however, it is difficult adequately to remove such material without damaging the newly formed, fresh granulation tissue. Partially granulating wounds of this type are frequently treated by repeatedly covering with and changing moist compresses. This is termed the "wet-to-dry principle".

There is a need in practice for a preparation which is suitable for the treatment, and in particular for cleaning and healing, infected wounds, for example wounds which are covered with pus and yellow necrosis, such as venous ulcera crures, post-traumatic wounds, deep burn wounds, gangrenous ulcers, decubitus and other exudative wounds. Disadvantages of known preparations are that a long-term treatment is frequently required and only moderate results are achieved.

These disadvantages are eliminated according to the invention. The invention relates specifically to the use of vegetable fibres or products derived therefrom originating from *Plantago ovata*, in particular from the seed husk thereof for the production of preparations for wound treatment. Such fibres and products derived therefrom are able to absorb moisture or to bind wound moisture, and to produce a mucus material in combination with moisture.

The polysaccharides originating from *Plantago ovata* which are used in the present invention contain a polyxylose basic structure and one or more side chains chosen from the group comprising galacturonic acid, galactose, mannose, glucose, fucose, ramnose and arabinose.

The expression "vegetable fibres or products derived therefrom originating from *Plantago ovata*, in particular from the seed husk thereof" comprises also products having the same, technically equivalent properties relating to the absorption or binding of (wound) moisture and the production of a mucous material in combination with moisture. Such products are in general vegetable materials, such as nutrient fibres and products derived therefrom in solid form.

Nutrient fibres are understood to be the constituents of plants which cannot be broken down or can be broken down only with difficulty by the human digestion system, in particular the digestive enzymes. When such fibres are consumed by man, they are not absorbed in the body and are excreted more or less unchanged with the faeces. Nutrient fibres occur, for example, in grain, vegetables and fruit. Other examples are Konjac mannan, pectin and guar. To date it is known that nutrient fibres of this type and the products derived therefrom contribute to improved bowel motions.

According to the invention it has therefore been found that products which contain vegetable fibres and in particular nutrient fibres or products derived from nutrient fibres and which to date are used to improve the bowel movements, can be used successfully for wound treatment.

It will be evident that the fibre material to be used according to the invention is initially preferably in dry, solid form. Thus, (dried) ground or granulated parts of plants (fibres) are suitable.

It has been found that exceptionally good results can be obtained using a so-called mucopolysaccharide, which originates from *Plantago ovata*, in particular from the seed husk thereof. The material concerned is a fibrous material, which is also termed Isphagula husk or psyllium (husk). It is known that psyllium fibres in finely ground form can be used successfully for the treatment of both diarrhoea and constipation. The preparations concerned are therefore volume-increasing preparations which are intended to be mixed with the bowel contents and which have the capacity for absorbing water. A soft, non-irritant filling of the bowel results, which restores the bowel action and promotes bowel movement. The use form generally comprises a pulverulent preparation, which is intended to be taken orally after dispersion in a liquid such as water.

It is to be noted as particularly surprising that the vegetable fibre materials defined above can be used in the field of wound treatment. Thus, for example, psyllium is found to have the following advantages when used in this way:

a non-specific binding occurs between the mucopolysaccharides and the cell walls of the bacteria present in the wound;

the mucopolysaccharides, which can be in the form of granules, absorb many times their own weight of water. Psyllium granules, for example, bind 4 times their weight of water;

there is a very gradual binding of moisture by the mucopolysaccharide, as a result of which painful pulling is avoided but the moisture-binding capacity occurs over a relatively long period;

a capillary action and a physical absorption occur because of the character of the particles and the space present in the mucopolysaccharide material.

It has been found that the vegetable fibres defined above and used according to the invention can be used successfully in combination with other (active) substances. In this context, other active substances can be chosen from the group comprising proteolytic enzymes, antiseptic agents, growth stimulators and electrolytes.

Proteolytic enzymes serve to break down undesired necrotic material in or around the wound to be treated. The antiseptic agents used can be the conventional agents suitable for wound treatment which have an antibacterial effect. Growth stimulators are known substances which promote the formation of granulation tissue and epithelium. One example of these substances is basic fibroblast growth factor. Electrolytes can also promote the action of the preparation containing (muco)polysaccharides; a suitable electrolyte is, for example, calcium citrate.

According to the invention, preparations are also provided which are suitable for use in the treatment of wounds of the type already indicated above. These preparations can be used both by the general practitioner, dermatologist, surgeon and other medical specialists and by the layman in the treatment of infected necrotic wounds.

The invention also relates to a preparation for wound treatment, comprising the vegetable fibres defined above together with an agent for application to the skin.

The polysaccharide materials preferably contain a polyxylose basic structure and one or more side chains chosen from the group comprising galactose, mannose, glucose, fucose, ramnose and arabinose. In particular, the preparation according to the invention contains psyllium, optionally together with the other active substances named above.

The preparation according to the invention is preferably in the form of a porous holder which can be applied to the skin. An example of a holder is, for example, a sachet or a compress-like product, which can have a surface area, which comes into contact with the skin, of, for example, 1-100 cm$^2$.

The porous holder enables interaction between wound moisture and polysaccharide material present in the holder. The pores of the holder must, of course, be such that the vegetable fibre material is retained in the holder to an appreciable extent. On the other hand, a small fraction of the mucopolysaccharide will, before or after moistening, penetrate through the pores of the holder and thus provide a mucus layer between the dermatological preparation and the wound which is being treated.

The preparation according to the invention preferably comprises a woven or nonwoven fleece material which itself also does not stick to the wound, so that no damage occurs when the dressing is changed. A suitable material is, for example, a polypropene fleece.

The preparation according to the invention can, for example, be in the form of a "cushion", which is formed from at least two fleeces applied on top of one another, at least one of which is porous. The cushion filling consists of vegetable fibre as defined in the above in the form of finely ground material, for example finely ground psyllium fibres. Cushions, for example having dimensions of 4×4 cm and containing 2.5 or 5 g of psyllium, can consist of two pieces of polypropene fleeces, which are joined together by ultrasonic welding or by other means.

The preparations according to the invention are outstandingly suitable for cleaning and healing wounds, examples of which have already been mentioned above. Because, in the case of the preparations according to the invention, gel formation takes place between the underside of the cushion and the wound surface, a moist medium is formed, as a result of which the preparation can also be used in the granulation tissue formation and epithelialisation stage.

The gel formation ensures that the dermatological preparation according to the invention, for example in the formation of a cushion, cannot stick to the wound surface, so that changing of the preparation is less painful and no or virtually no damage occurs to newly formed tissue. The jelly-like layer has an occlusive action, as a result of which the pain in the wound decreases after application of the preparation according to the invention.

After application of the preparation according to the invention to the wound, wound exudate, pus, bacteria and fragmented necrotic material will be absorbed and retained by the preparation.

After applying a dry preparation according to the invention, wound moisture slowly penetrates through the pores (meshes) of the holder (fleece material) and as a result of this a moist physiological medium is maintained on the wound surface, which promotes optimal wound healing.

The invention also relates to a method for the treatment of skin disorders of the abovementioned type using the vegetable fibers or products derived therefrom defined above, or the preparations defined above.

As already mentioned, the preparations according to the invention can be used successfully in the cleaning stage and granulation stage and in the epithelialisation stage.

In the cleaning stage it is important to remove any black necrosis present before a clean and dry preparation according to the invention is applied. Depending on the size of the wound, one or more preparations according to the invention will, in a sterile manner, be placed in the wound and pressed on well, so that there is optimum contact with the bottom of the wound. As a result of the absorbent characteristics, exudate, pus, bacteria and necrosis residues are absorbed and retained, so that there is a decrease in the yellow coating each time the preparation is changed. The preparations according to the invention (for example in the form of cushions) can be held in place by a single hydrophillic bandage.

In the case of highly exudative wounds, replacement of the preparation once every 24 hours is desirable. Thereafter, changing has to take place only, for example, once every two or three days. Consequently, the preparation can be outstandingly combined with elastic and non-elastic compression for the treatment of veneus ulcus cruris. In the granulation stage, the preparation is applied in the same way.

Factors which have a favourable influence on the wound-healing are present in the moist wound medium of the jelly layer between preparation according to the invention and wound surface.

An important practical advantage of the preparations according to the invention is that they have to be changed only infrequently, that virtually no damage occurs to newly formed tissue and, finally, excellent and cosmetically highly acceptable scarring takes place.

The amount in which the vegetable fibres, according to the invention is used is not critical. A preparation in cushion form can, for example, have dimensions of 4—4 cm and contain 5 g of psyllium granules. As already suggested above, any shape is conceivable and preparations consisting of more than one cushion can also be considered. The amount of granules is, of course, dependent on the surface to be treated. The amounts and sizes can easily be determined by the attendant physician on the basis of the size and the nature of the wound.

The invention is illustrated in more detail in the following test report.

TEST REPORT

Introduction

The cleaning effect of psyllium cushions in the case of patients suffering from necrotic venous leg ulcers (venous ulcera crures) was investigated. The results were evaluated by means of visual observation, morphometric analysis and computer image analysis gives of Polaroid photographs of the ulcers. As the computer image analysis gives the best, reproducible and objective results, these data are used for further analysis. The results can be compared with the results obtained in accordance with the standard treatment (15 patients) and a treatment which makes use of proteolytic enzymes originating from antarctic krill (22 patients), which were evaluated in the same period using the same computer methods.

Materials and Methods

Each psyllium cushion contains 2.5 g of granules and is able to absorb a maximum of 10 ml of water. The cushions were fixed loosely using a hydrophillic gauze bandage. The cushions were changed once per day. The exudate was absorbed well by the cushions. The jelly-like material which leaked out of the cushions was carefully removed from the ulcer every day and the adjoining skin was rinsed with a saline solution. The wound surface area was drawn on a transparent sheet before and after the treatment.

The effectiveness of the treatment was determined by the physician and by the patient using a scale (see Table 1) which runs from 1 (good result) to 4 (no result). The qualitative aspects, that is to say the percentage of the region where granulation tissue was present, were roughly estimated visually every day using a scale of 1 to 5 (0-20%, 21-40%, 41-60%, 61-80%, 81-100%). To supplement these estimates, photographs were taken daily using a fixed-focus Polaroid camera (Acmel). The black/yellow region (necrosis) and the red region (granulation tissue) were measured by means of morphometric analysis and computer image analysis of the Polaroid photographs. For this purpose a metric grey scale was fixed close to the wound in order to ensure absolute measurement of size and colour in the computer evaluation. The total wound region was also measured directly from the transparent sheets using a computer.

Before and during the treatment, the patient was asked whether the treatment caused pain or gave rise to any other complaint. Pain and discomfort were rated on a scale of 1 to 4. The presence of clinical infection symptoms, such as erythema, warm to the touch, oedema or pus formation, were rated with the aid of a scale from 1 to 3. Side effects were recorded if present. In addition, the medical history, prior and current treatments and duration of the ulcer were recorded.

Patients

This report covers a total of 6 necrotic venous ulcers. The average duration of the ulcer was 5.2 months.

Exclusion criteria were: pregnancy arterial insufficiency (defined as "a single-pulse index below 0.7"), vasculitis, peripheral neuropathy or diabetes. The single-pulse index was measured for each patient. The maximum wound size was determined by the size of the cushions, 5×5 cm, but it was possible to treat larger ulcers by using 2 cushions lying alongside one another. This was necessary in the case of patient No. 4 (size of the ulcer 9×5 cm, 2 cushions used).

Results

All ulcers were ready for transplant after 7 days.

The reduction in the amount of necrotic tissue in the course of one week is shown in FIG. 1. The same data, expressed in percentages of the total yellow region on day 0, are shown in FIG. 1b. The total wound region declined by on average 4.5% in the psyllium group.

With regard to the cleaning effect, that is to say reduction in the yellow area, an average reduction of 55% was found for the treatment with psyllium after treating for 7 days (FIG. 2).

The overall assessment of the effect by the investigator and by the patient is indicated in Table 2.

Both treatments effect approximately the same reduction in pain. Symptoms relating to the wound, such as oedema and erythema around the ulcers were alleviated and no signs of side effects were found. It can be seen from FIG. 3 that the wound-cleaning effect is comparable with that of 6.0 U/ml of krill enzymes, which were applied twice per day with occlusion, and is appreciably better than the control treatment with a saline solution (n=15). FIG. 4 shows the effect of psyllium in comparison with krill enzymes (6.0 U/ml), for the same period and tested and evaluated by the same investigator (n=5). The difference is not significant but also indicates that the effect is approximately the same.

Discussion

In the case of 6 patients a clean, granulating wound surface which is suitable for skin transplant was obtained by applying highly absorbent psyllium gauze cushions once per day for a period of 7 days, which treatment reduce the necrosis by 55% (55% of the amount of necrosis measured on day 0). This is regarded as a good result compared with other treatments such as repeated changing of dressings saturated with a saline solution or commercially available enzymatic products.

There was no significant reduction in the total wound area, but this can also not be expected during a treatment of only one week.

Compared with the standard treatment, which consists of changing dressings saturated with a saline solution three times per day, the use of psyllium cushions saves time.

In conclusion, it can be stated that these simple absorbent psyllium cushions meet the requirements with regard to effectiveness and easy handling of débridement of venous leg ulcers.

TABLE 1

Description of the Recording System

Overall rating of the evaluation by the physician
1. good result (clean wound, good granulation tissue, no bacterial contamination)
2. reasonable (not completely clean, good granulation, no bacterial contamination)
3. just clean enough to carry out the transplant
4. not clean enough to carry out the transplant.
Overall rating of the evaluation by the patient
1. clearly much cleaner than before the treatment
2. cleaner than before the treatment
3. no difference or very little difference
4. worse than before the treatment
Clinical signals of infection
1. very little pus formation, no odour or erythema, not warm to the touch and no oedema.
2. some pus formation, some exudate, some odour, some erythema, somewhat warm to the touch or some oedema.
3. abundant pus formation, exudate and odour, erythema, pain, heat, oedema.
Pain
1. not painful
2. hardly painful
3. somewhat painful, some pain
4. very painful
Discomfort from the dressing method
1. very comfortable
2. comfortable
3. fairly comfortable 4. uncomfortable Formation of granulation tissue
1. 0–20%
2. 21–40%
3. 41–60%
4. 61–80%
5. 81–100%

TABLE 2

| pysllium | Granulation assessment (5 = good) | | Overall result (1 = good) | | Clinical infection symptoms | | Pain | | Treatment comfort | |
|---|---|---|---|---|---|---|---|---|---|---|
| | day 0 | day 7 | physician day 7 | patient day 7 | day 0 | day 7 | day 0 | day 7 | day 2 | day 7 |
| 1 | 1 | 5 | 1 | 1 | 3 | 3 | 2 | 2 | 2 | 2 |
| 2 | 5 | 1 | 1 | 2 | 1 | 3 | 1 | 2 | 2 | |
| 3 | 2 | 5 | 2 | 2 | 2 | 2 | 2 | 1 | 2 | 1 |
| 4 | 1 | 4 | 2 | 2 | 2 | 1 | 3 | 1 | 1 | 1 |
| 5 | 1 | 3 | 3 | 2 | 2 | 2 | 1 | 1 | 1 | 1 |
| 6 | 1 | 4 | 1 | — | 2 | 1 | 2 | 1 | 2 | 2 |
| average | 1.5 | 4.33 | 1.67 | 1.6 | 2.17 | 1.67 | 2.17 | 1.17 | 1.67 | 1.5 |

Figure 1A:
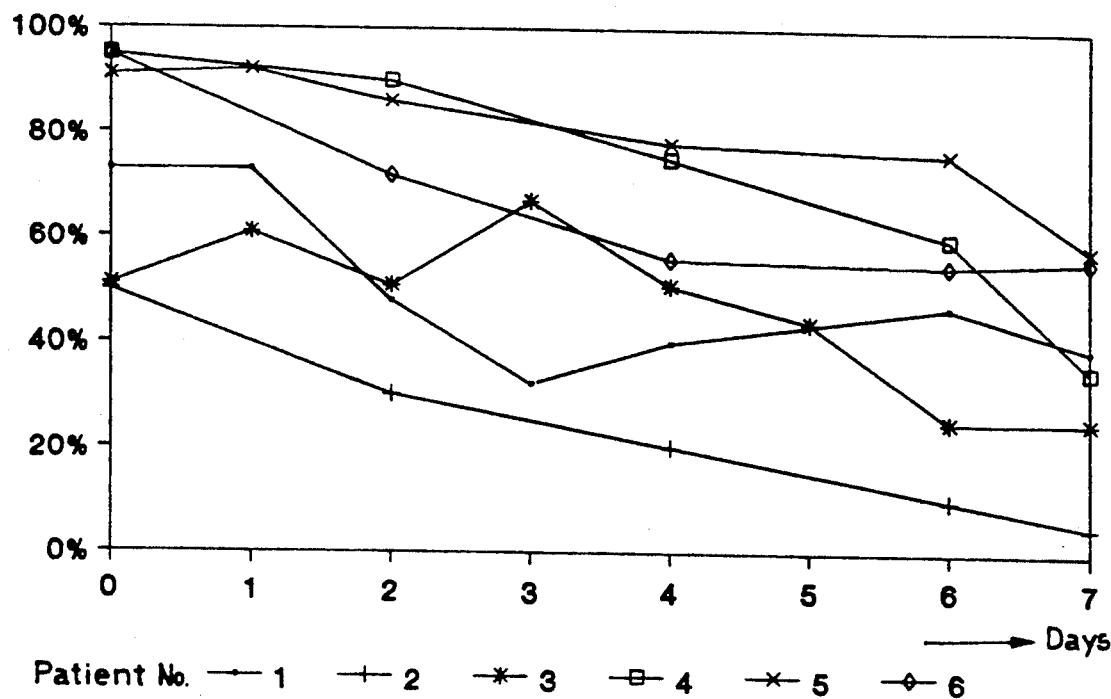
FIG. 1a: This figure shows the wound-cleaning effect of psyllium for 6 patients over a period of 7 days. The decrease in the amount of necrotic tissue is indicated.
Figure 1B:
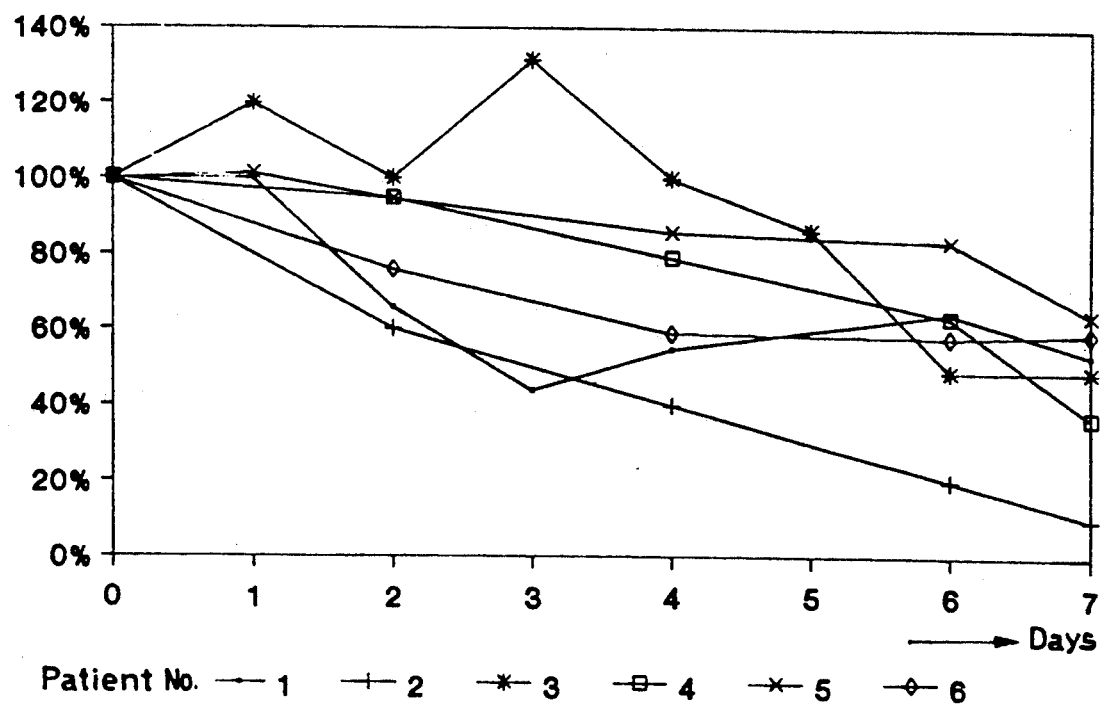
FIG. 1b: This figure corresponds to FIG. 1a, but the wound-cleaning effect is expressed as a percentage of the total yellow area on day 0.
Figure 2:
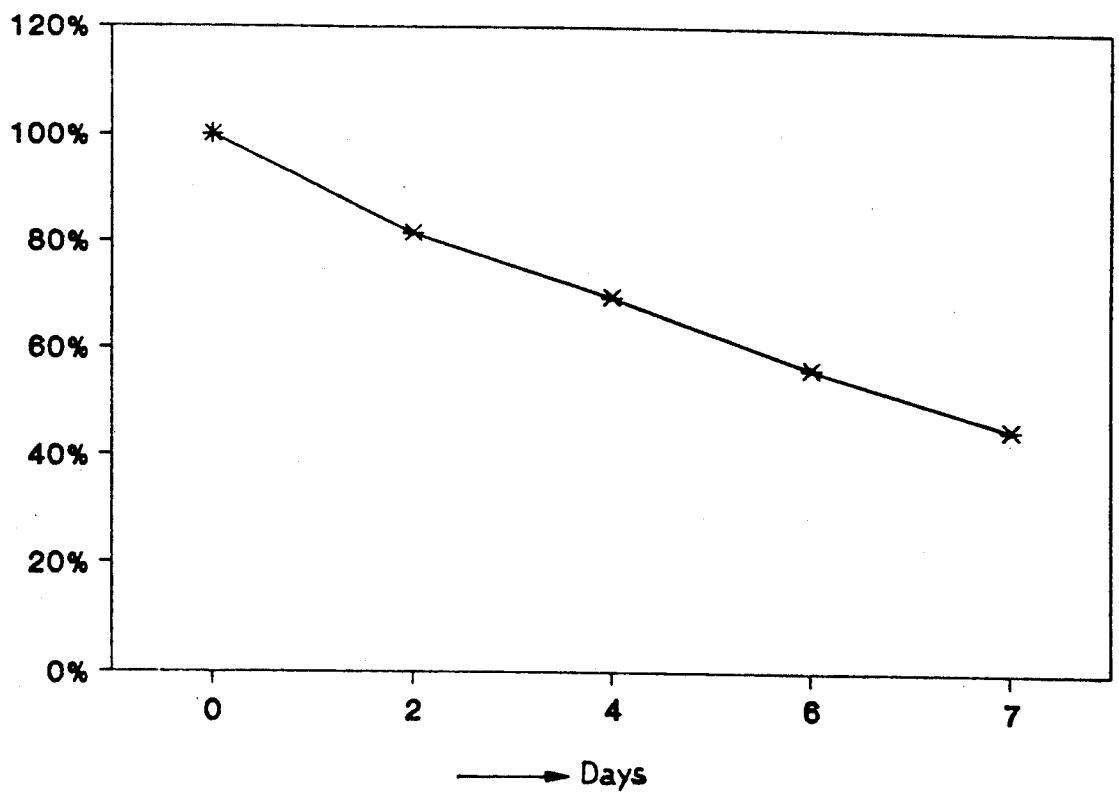
FIG. 2: In this figure the necrotic area over a period of 7 days, expressed as a percentage relative to day 0, is shown for 6 patients.
Figure 3:
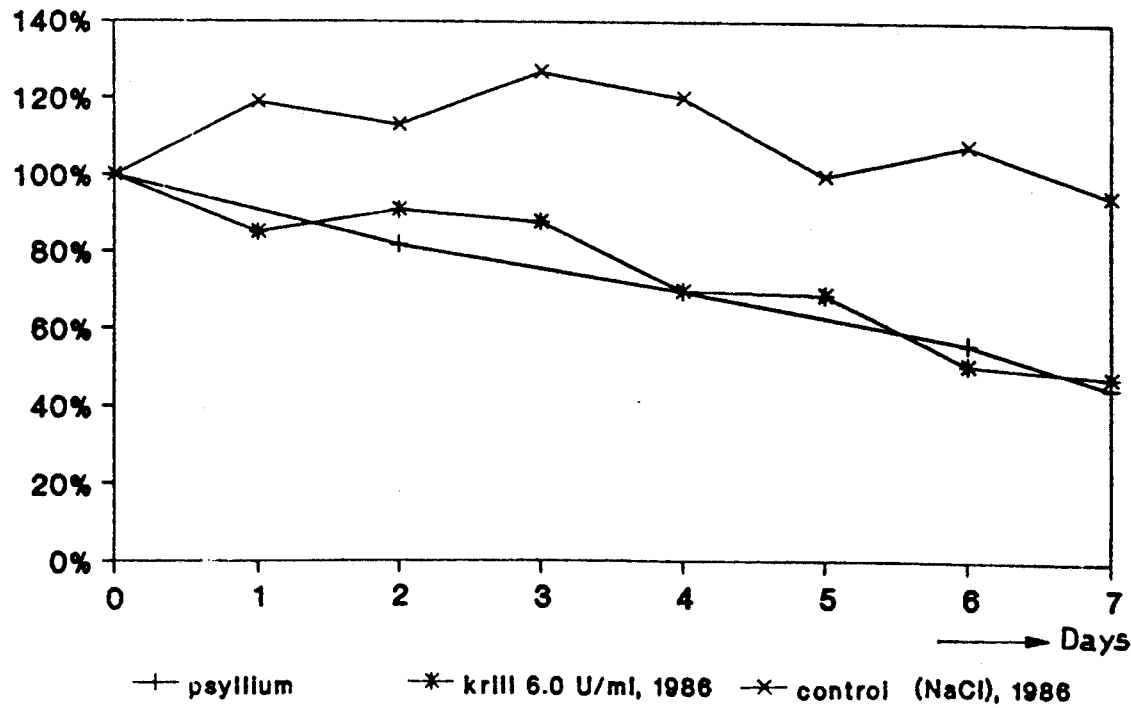
FIG. 3: This figure shows that over a period of 7 days the decrease in the necrosis in the case of the patients studied is comparable with that for the treatments treated with krill enzymes. The decrease in necrosis is indicated as a percentage relative to day 0. The number of patients is 15.
Figure 4:
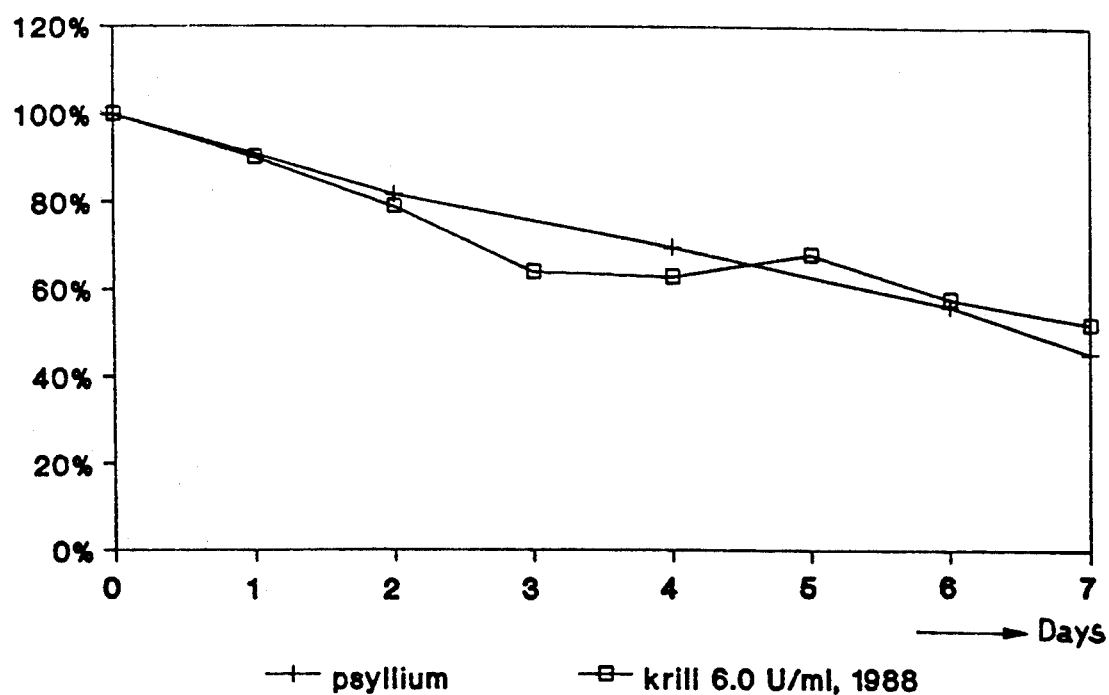
FIG. 4: This figure corresponds to FIG. 3, the effect of psyllium on a group of 5 patients being compared with the effect of krill enzyme, the study being carried out for the same period and by the same investigator.

We claim:

1. Process for wound treatment which comprises applying to the wound of an affected patient a vegetable fiber material originating from *Plantago ovata*.

2. Process according to claim 1 wherein said material is used in combination with an active substance selected from the group consisting of proteolytic enzymes, antiseptic agents, growth stimulators and electrolytes.

3. Process according to claim 1 wherein said material originates from the seed husk of *Plantago ovata*.

4. Process according to claim 1 wherein said material is applied to wounds which are covered by pus and yellow necrosis.

5. Preparation for wound treatment which comprises a vegetable fiber material originating from *Plantago ovata*, together with holder for application to the skin.

6. Preparation according to claim 5 in combination with an active substance selected from the group consisting of proteolytic enzymes, antiseptic agents, growth stimulators and electrolytes.

7. Preparation according to claim 5 wherein said material originates from the seed husk of *Plantago ovata*.

8. Preparation according to claim 5 in the form of a porous holder which can be applied to skin.

9. Preparation according to claim 8 in which the holder comprises a woven or nonwoven fleece material which does not adhere to the wound.

10. Preparation according to claim 9 in which the fleece material comprises a polypropene fleece.

* * * * *